(12) United States Patent
Leo et al.

(10) Patent No.: US 9,746,414 B2
(45) Date of Patent: Aug. 29, 2017

(54) METHOD AND SYSTEM FOR ESTIMATING THE POTENTIAL FRICTION BETWEEN A VEHICLE TYRE AND A ROLLING SURFACE

(71) Applicant: PIRELLI TYRE S.P.A., Milan (IT)

(72) Inventors: Elisabetta Leo, Lecco (IT); Marco Ezio Pezzola, Lecco (IT)

(73) Assignee: PIRELLI TYRE S.P.A., Milan (IT)

( * ) Notice: Subject to any disclaimer, the term of this patent is extended or adjusted under 35 U.S.C. 154(b) by 0 days.

(21) Appl. No.: 14/896,092

(22) PCT Filed: Jun. 12, 2014

(86) PCT No.: PCT/IB2014/062159
§ 371 (c)(1),
(2) Date: Dec. 4, 2015

(87) PCT Pub. No.: WO2014/199328
PCT Pub. Date: Dec. 18, 2014

(65) Prior Publication Data
US 2016/0123866 A1 May 5, 2016

(30) Foreign Application Priority Data
Jun. 14, 2013 (IT) .............................. MI2013A0983

(51) Int. Cl.
*G01N 19/02* (2006.01)
*B60T 8/17* (2006.01)
(Continued)

(52) U.S. Cl.
CPC .............. *G01N 19/02* (2013.01); *B60T 8/172* (2013.01); *B60W 40/068* (2013.01); *G01M 17/02* (2013.01); *B60T 2210/12* (2013.01)

(58) Field of Classification Search
CPC ...... B60T 2210/12; B60T 8/172; G01N 19/02
(Continued)

(56) References Cited
U.S. PATENT DOCUMENTS 3,825,304 A * 7/1974 Kiatipoff ............. B60T 8/17613
188/181 C
5,015,041 A * 5/1991 Kuwana .............. B60T 8/17616
188/181 C
(Continued)

FOREIGN PATENT DOCUMENTS

CN          1678472 A     5/2005
CN        102791546 A    11/2012
(Continued)

OTHER PUBLICATIONS

International Search Report from the European Patent Office for International Application No. PCT/IB2014/062159, mailing date Oct. 8, 2014.
(Continued)

*Primary Examiner* — Randy Gibson
*Assistant Examiner* — Gedeon M Kidanu
(74) *Attorney, Agent, or Firm* — Finnegan, Henderson, Farabow, Garrett & Dunner, L.L.P.

(57) ABSTRACT

A method and system for estimating the potential friction between a tire and a rolling surface in which: a first and second engaged-friction/kinematic-quantity reference curve respectively corresponding to a first and to a second reference value $\mu\rho_1$, $\mu_{P2}$ of potential friction with $\mu_{P2} > \mu_{P1}$ are provided; a first and a second kinematic quantity threshold value or a first and a second engaged friction threshold value are provided; the engaged friction $\mu$ between the tire and the rolling surface is determined; a current value of a kinematic quantity between the tire and the rolling surface is determined; a current working point given by the engaged friction $\mu$ and the current value of the kinematic quantity is determined; and the current value of the kinematic quantity is compared with the first and the second kinematic quantity threshold value or, respectively, the engaged friction $\mu$ is
(Continued)

compared with the first and the second engaged friction threshold value.

29 Claims, 9 Drawing Sheets

(51) Int. Cl.
  *B60T 8/172* (2006.01)
  *B60W 40/068* (2012.01)
  *G01M 17/02* (2006.01)

(58) Field of Classification Search
  USPC .................................................. 73/9
  See application file for complete search history.

(56) References Cited

U.S. PATENT DOCUMENTS

| | | | |
|---|---|---|---|
| 6,094,614 A | | 7/2000 | Hiwatashi |
| 6,662,898 B1 * | | 12/2003 | Mattson .............. B60G 17/0195 180/402 |
| 8,645,038 B2 | | 2/2014 | Kammann et al. |
| 2002/0111752 A1 | | 8/2002 | Nakamura |
| 2004/0032165 A1 | | 2/2004 | Levy et al. |
| 2004/0049303 A1 * | | 3/2004 | Levy ..................... B60C 11/24 700/80 |
| 2005/0085987 A1 * | | 4/2005 | Yokota ................ B60C 23/0477 701/80 |
| 2005/0234628 A1 * | | 10/2005 | Luders ................. B60T 8/1725 701/80 |
| 2005/0246087 A1 | | 11/2005 | Hommi et al. |
| 2008/0228411 A1 * | | 9/2008 | Miyashita .............. B60C 19/00 702/34 |
| 2010/0114449 A1 * | | 5/2010 | Shiozawa ................ B60L 3/10 701/90 |
| 2011/0015906 A1 * | | 1/2011 | Bian ...................... B60T 8/172 703/2 |
| 2011/0166761 A1 | | 7/2011 | Kammann et al. |
| 2011/0209521 A1 * | | 9/2011 | Shiozawa ............... B60L 3/102 73/9 |
| 2011/0264300 A1 | | 10/2011 | Tuononen |
| 2012/0179327 A1 * | | 7/2012 | Yngve ................ B60W 40/064 701/32.9 |
| 2012/0323459 A1 | | 12/2012 | Okubo |

FOREIGN PATENT DOCUMENTS

| | | |
|---|---|---|
| DE | 10 2010 048 927 | 4/2011 |
| DE | 102010004113 A1 | 7/2011 |
| EP | 0 444 772 | 9/1991 |
| EP | 1 510 428 | 3/2005 |
| JP | 5-016780 | 1/1993 |
| JP | H06-40051 B | 5/1994 |
| JP | 2002-154418 A | 5/2002 |
| JP | 2004-249965 A | 9/2004 |
| JP | 2012-503192 A | 2/2012 |
| WO | WO 2010/031905 A1 | 3/2010 |

OTHER PUBLICATIONS

Written Opinion of the International Searching Authority from the European Patent Office for International Application PCT/IB2014/062159, mailing date Oct. 8, 2014.

Office Action issued Aug. 25, 2016 by the State Intellectual Property Office of the People's Republic of China in corresponding Application No. 201460039675.5.

Notice of Reasons for Rejection issued Jul. 15, 2016 by the Japan Patent Office in corresponding Application No. JP 2015-563044 (3 pages).

English-language translation of Notice of Reasons for Rejection issued Jul. 15, 2016 by the Japan Patent Office in corresponding Application No. JP 2015-563044 (4 pages).

\* cited by examiner

| Wet granite – right front wheel - $\mu_p = 0.2$ | | | | |
|---|---|---|---|---|
| | $\varepsilon<0.7\%$ | $0.7\%\leq\varepsilon<1.2$ | $\varepsilon\geq1.2\%$ | TOTAL |
| N° wheel revolutions % | 357 32% | 391 35% | 365 33% | 1113 100% |
| VL $\mu_p \leq 0.2$ | N.A | 390 99,74% | 347 95,07% | |
| L $0.2 < \mu_p \leq 0.4$ | | | 18 4,93% | |
| NVL $\mu_p > 0.2$ | | 1 0.26% | | |
| NL $\mu_p > 0.4$ | | | 0 0,00% | |

Fig. 5

| Dry cement – right front wheel - $\mu_p = 0.85$ | | | | |
|---|---|---|---|---|
| | $\varepsilon<0.7\%$ | $0.7\%\leq\varepsilon<1.2$ | $\varepsilon\geq1.2\%$ | TOTAL |
| N° wheel revolutions % | 299 28% | 719 67% | 52 5% | 1070 100% |
| VL $\mu_p \leq 0.2$ | N.A. | 5 0,70% | 0 0,00% | |
| L $0.2 < \mu_p \leq 0.4$ | | | 0 0,00% | |
| NVL $\mu_p > 0.2$ | | 714 99,30% | | |
| NL $\mu_p > 0.4$ | | | 52 100,00% | |

Fig. 6a

| Dry cement – right front wheel - $\mu_p = 0.85$ | | | |
|---|---|---|---|
| | $\varepsilon<0.7\%$ | $0.7\%\leq\varepsilon<1.2$ | $\varepsilon\geq1.2\%$ | TOTAL |
| N° wheel revolutions % | 299 / 28% | 719 / 67% | 52 / 5% | 1070 / 100% |
| VL $\mu_p \leq 0.2$ | N.A. | 3 / 0,42% | 0 / 0,00% | |
| L $0.2<\mu_p\leq0.4$ | | | 0 / 0,00% | |
| NVL $\mu_p>0.2$ | | 716 / 99,58% | | |
| NL $\mu_p>0.4$ | | | 52 / 100,00% | |

Fig. 6b

METHOD AND SYSTEM FOR ESTIMATING THE POTENTIAL FRICTION BETWEEN A VEHICLE TYRE AND A ROLLING SURFACE

CROSS REFERENCE TO RELATED APPLICATIONS

This application is a national phase application based on PCT/IB2014/062159, filed Jun. 12, 2014, which claims the priority of Italian Patent Application No. MI2013A000983, filed Jun. 14, 2013, the content of both applications being incorporated herein by reference.

BACKGROUND OF THE INVENTION

Field of the Invention

The invention relates to a method and a system for estimating the potential friction between a vehicle tyre and a rolling surface.

Description of the Related Art

Systems for estimating the potential friction are known in the art. See, for example, documents US 2011/0166761, US 2012/0179327, US 2011/0264300, EP 0 444 772, EP 1 510 428, U.S. Pat. No. 6,094,614.

In the present description and claims, "potential friction" is meant to indicate the ordinate of the absolute maximum point in an engaged-friction/kinematic-quantity curve. The kinematic quantity can be the (longitudinal) slip or the drift angle. In the first case, the engaged friction is defined as the ratio between the longitudinal force $F_x$ exchanged in the plane of contact between the tyre and the rolling surface and the vertical load $F_z$ acting on the tyre. In the second case, the engaged friction is defined as the ratio between the lateral force $F_y$ exchanged in the plane of contact between the tyre and the rolling surface and the vertical load $F_z$ acting on the tyre.

In the present description and claims, "engaged-friction/kinematic-quantity curve" is meant to indicate a curve with a predetermined uncertainty band such as to take into account the dispersion of experimental data of engaged friction and kinematic quantity.

In the present description and claims, transitory rolling condition is meant to indicate a substantially rectilinear rolling condition in acceleration or braking; a condition of cornering at constant speed; or a condition of cornering in acceleration or braking, preferably not extreme.

In the present description, "free rolling" condition is meant to indicate a substantially stationary rolling condition, in the substantial absence of longitudinal and/or lateral forces applied to the tyre.

In the present description and claims:
the terms "lateral" and "laterally" are used to indicate quantities measured in a direction substantially parallel to the rotation axis of the tyre;
the terms "radial" and "radially" are used to indicate quantities measured in a direction substantially perpendicular to the rotation axis of the tyre, i.e. in a direction that intersects the rotation axis of the tyre and lies in a plane perpendicular to such a rotation axis;
the terms "longitudinal" and "longitudinally" are used to indicate quantities measured tangentially to the tyre and substantially perpendicular to the lateral direction and to the radial direction (i.e. in the direction of forward motion of the tyre/vehicle).

With the varying of the conditions of a tyre-rolling surface system, in other words the operating conditions of the tyre (for example vertical load acting on the tyre, inflation pressure of the tyre, speed, wear, temperature, etc.), the characteristics of the tyre itself (structure, tread compound, etc.), and/or the characteristics and conditions of the rolling surface (presence of slippery elements like snow, ice, leaves, roughness, etc.), the relationship between engaged friction and kinematic quantity is described by a different curve and correspondingly there is a different potential friction.

FIG. 1 represents three examples of engaged friction $(F_x/F_z)$/slip ($\epsilon$) curves for three different conditions of tyre-rolling surface (granite, cement and asphalt) system.

In practice, the potential friction identifies a limit condition beyond which the adherence conditions of the tyre begin to degrade, up to an asymptotic condition in which, as the slip increases, the engaged friction remains substantially constant and less than the maximum friction (i.e. the potential friction itself).

In each engaged-friction/kinematic-quantity curve it is possible to substantially identify three regions: linear, non-linear and asymptotic (see regions A, B, C, respectively, in FIG. 1).

The linear region represents substantially a "free rolling" or "steady state" condition in which the engaged friction increases substantially linearly as the kinematic quantity increases. In this region the engaged-friction/kinematic-quantity curves relating to different conditions of the tyre-rolling surface system tend to concentrate close to the origin, practically overlapping one another, so as not to be discerned from one another due to the inevitable characteristic uncertainty of the measurements from which the slip and the engaged friction are obtained.

The asymptotic region represents the aforementioned asymptotic condition in which, as the kinematic quantity increases, the engaged friction remains substantially constant.

The non-linear region represents substantially a transitory rolling condition in which the engaged friction increases substantially non-linearly as the kinematic quantity increases. In this region the engaged-friction/kinematic-quantity curves separate from one another.

SUMMARY OF THE INVENTION

The Applicant has observed that there is no correlation between slope of the linear region and potential friction. In other words, it may be the case that a curve with a greater slope in the linear region then has a lower potential friction with respect to another curve with a lesser slope. The Applicant has, however, observed that, despite this, the curves with lower potential friction pass from the linear to the non-linear region ahead of the curves with higher potential friction. In other words, curves with lower potential friction separate and become distinguishable in advance of other curves, thus having a relatively short linear region.

Based on this observation, the Applicant has found that by selecting kinematic quantity and/or engaged friction thresholds at points in which engaged-friction/kinematic-quantity reference curves become substantially distinguishable from respective reference curves at higher potential friction and by comparing engaged-friction/kinematic-quantity working points with such thresholds and such reference curves, it is possible to obtain information on the potential friction as soon as the reference curve at lower potential friction becomes distinguishable from the other reference curves and then ever more precise information as the other reference curves also become distinguishable from the respective reference curves at higher potential friction, as the current values of engaged friction and/or kinematic quantity increase.

In a first aspect thereof, the present invention therefore concerns a method of estimating the potential friction $\mu_p$ between a tyre and a rolling surface.

The estimating method can operate on kinematic quantity thresholds and/or on engaged friction thresholds.

In the case of use of kinematic quantity thresholds, the estimating method comprises:
  providing a first and a second engaged-friction/kinematic-quantity reference curve respectively corresponding to a first and to a second reference value $\mu_{p1}$, $\mu_{p2}$ of potential friction with $\mu_{p2} > \mu_{p1}$;
  providing a first and a second kinematic quantity threshold value, said first threshold value corresponding to a kinematic quantity value in which said first reference curve is substantially distinguishable from said second reference curve, and said second threshold value corresponding to a kinematic quantity value in which said second reference curve is substantially distinguishable from at least one third reference curve corresponding to a third reference value $\mu_{p3}$ of potential friction with $\mu_{p3} > \mu_{p2}$;
  determining the engaged friction p, between the tyre and the rolling surface;
  determining a current value of a kinematic quantity between the tyre and the rolling surface;
  determining a current working point given by the engaged friction $\mu$ and the current value of the kinematic quantity;
  comparing the current value of the kinematic quantity with the first and the second kinematic quantity threshold value;
  if the current value of the kinematic quantity is comprised between the first and the second kinematic quantity threshold value and said working point is above said first reference curve, determining that the value of the potential friction is greater than said first reference value $\mu_{p1}$;
  if the current value of the kinematic quantity is greater than the second kinematic quantity threshold value and said working point is above said second reference curve, determining that the value of the potential friction is greater than said second reference value $\mu_p$ of potential friction;
  if the current value of the kinematic quantity is greater than the second kinematic quantity threshold value and said working point is comprised between said first and said second reference curve, determining that the value of the potential friction is comprised between said first reference value $\mu_{p1}$ of potential friction and said second reference value $\mu_{p2}$ of potential friction;
  if the current kinematic quantity is greater than the first kinematic quantity threshold value and said working point is not above said first reference curve, determining that the value of the potential friction is equal to or less than said first reference value $\mu_{p1}$.

In the case of use of engaged friction thresholds, the estimating method comprises:
  providing a first and a second engaged-friction/kinematic-quantity reference curve respectively corresponding to a first and to a second reference value $\mu_{p1}$, $\mu_{p2}$ of potential friction with $\mu_{p2} > \mu_{p1}$;
  providing a first and a second engaged friction threshold value, said first threshold value corresponding to an engaged friction value in which said first reference curve is substantially distinguishable from said second reference curve, and said second threshold value corresponding to an engaged friction value in which said second reference curve is substantially distinguishable from at least one third reference curve corresponding to a third reference value $\mu_{p3}$ of potential friction with $\mu_{p3} > \mu_{p2}$;
  determining the engaged friction $\mu$ between the tyre and the rolling surface;
  determining a current value of a kinematic quantity between the tyre and the rolling surface;
  determining a current working point given by the engaged friction $\mu$ and the current value of the kinematic quantity;
  comparing the engaged friction $\mu$ with the first and the second engaged friction threshold value;
  if the engaged friction $\mu$ is comprised between the first and the second engaged friction threshold value and said working point is above said first reference curve, determining that the value of the potential friction is greater than said first reference value $\mu_{p1}$;
  if the engaged friction $\mu$ is greater than the second engaged friction threshold value and said working point is above said second reference curve, determining that the value of the potential friction is greater than said second reference value $\mu_{p2}$ of potential friction;
  if the engaged friction $\mu$ is greater than the second engaged friction threshold value and said working point is comprised between said first and said second reference curve, determining that the value of the potential friction is comprised between said first reference value $\mu_{p1}$ of potential friction and said second reference value $\mu_{p2}$ of potential friction;
  if the engaged friction $\mu$ is greater than the first engaged friction threshold value and said working point is not above said first reference curve, determining that the value of the potential friction is equal to or less than said first reference value $\mu_{p1}$.

In a second aspect thereof, the present invention concerns a system for estimating the potential friction between a tyre and a rolling surface comprising:
  a memory wherein a first and a second engaged-friction/kinematic-quantity reference curve are stored, respectively corresponding to a first and to a second reference value $\mu_{p1}$, $\mu_{p2}$ of potential friction with $\mu_{p2} > \mu_{p1}$; and a first and a second kinematic quantity threshold value, or a first and a second engaged friction threshold value; said first threshold value corresponding to a kinematic quantity value or, respectively, engaged friction value in which said first reference curve is substantially distinguishable from said second reference curve, and said second threshold value corresponding to a kinematic quantity value or, respectively, engaged friction value in which said second reference curve is substantially distinguishable from at least one third reference curve corresponding to a third reference value $\mu_{p3}$ of potential friction with $\mu_{p3} > \mu_{p2}$;
  at least one processing module configured to:
  determine the engaged friction $\mu$ between the tyre and the rolling surface;
  determine a current value of a kinematic quantity between the tyre and the rolling surface;
  determine a current working point given by the engaged friction $\mu$ and the current value of the kinematic quantity;
  comparing the current value of the kinematic quantity with the first and the second kinematic quantity threshold value or, respectively, the engaged friction μ with the first and the second engaged friction threshold value;

if the current value of the kinematic quantity or the engaged friction μ is comprised between the respective first and second threshold value and said working point is above said first reference curve, determining that the value of the potential friction is greater than said first reference value $\mu_{p1}$;

if the current value of the kinematic quantity or the engaged friction μ is greater than the respective second threshold value and said working point is above said second reference curve, determining that the value of the potential friction is greater than said second reference value $\mu_{p2}$ of potential friction;

if the current value of the kinematic quantity or the engaged friction μ is greater than the respective second threshold value and said working point is comprised between said first and said second reference curve, determining that the value of the potential friction is comprised between said first reference value $\mu_{p1}$ of potential friction and said second reference value $\mu_{p2}$ of potential friction;

if the current kinematic quantity or the engaged friction μ is greater than the respective first threshold value and said working point is not above said first reference curve, determining that the value of the potential friction is equal to or less than said first reference value $\mu_{p1}$.

The present invention in at least one of the aforementioned aspects can have at least one of the following preferred characteristics.

Preferably, said first engaged-friction/kinematic-quantity reference curve is selected so as to correspond to a reference value $\mu_{p1}$ of potential friction less than or equal to 0.3.

Preferably, said first engaged-friction/kinematic-quantity reference curve is selected so as to correspond to a reference value $\mu_{p1}$ of potential friction at least equal to 0.15.

Preferably, said second engaged-friction/kinematic-quantity reference curve is selected so as to correspond to a reference value $\mu_{p2}$ of potential friction comprised between 0.35 and 0.5.

Preferably, said at least one third engaged-friction/kinematic-quantity reference curve is selected so as to correspond to a reference value $\mu_{p3}$ of potential friction at least equal to 0.55.

Preferably, the first engaged friction threshold value is less than the first reference value $\mu_{p1}$ of potential friction.

Preferably, the first reference curve is selected so that the first engaged friction threshold value is comprised between 0.05 and 0.2.

Preferably, the second engaged friction threshold value is greater than the first reference value $\mu_{p1}$ of potential friction and less than the second reference value $\mu_{p2}$ of potential friction.

Preferably, the second reference curve is selected so that the second engaged friction threshold value is comprised between 0.25 and 0.4.

In a preferred embodiment, both the first and the second kinematic quantity threshold value and the first and the second engaged friction threshold value are provided and, if the current value of the kinematic quantity is less than the first kinematic quantity threshold value:

if the engaged friction μ is comprised between said first and said second engaged friction threshold value, determining that the value of the potential friction is greater than said first reference value $\mu_{p1}$ of potential friction;

if the engaged friction μ is greater than said second engaged friction threshold value, determining that the value of the potential friction is greater than said second reference value $\mu_{p2}$ of potential friction.

In this preferred embodiment, if the current value of the kinematic quantity is comprised between the first and the second kinematic quantity threshold value and if the engaged friction μ is greater than said second engaged friction threshold value, preferably it is determined that the value of the potential friction is greater than said second reference value $\mu_{p2}$ of potential friction.

In a preferred embodiment, both the first and the second kinematic quantity threshold value and the first and the second engaged friction threshold value are provided and, if the engaged friction is less than the first engaged friction threshold value:

if the current value of the kinematic quantity is greater than the first kinematic quantity threshold value, determining that the value of the potential friction is equal to or less than said first reference value $\mu_{p1}$.

In this preferred embodiment, if the engaged friction is comprised between the first and the second engaged friction threshold value and if the current value of the kinematic quantity is greater than the second kinematic quantity threshold value and the working point is above said first reference curve, preferably it is determined that the value of the potential friction is comprised between said first reference value $\mu_{p1}$ and said second reference value $\mu_{p2}$ of potential friction.

In a preferred embodiment, both the first and the second kinematic quantity threshold value and the first and the second engaged friction threshold value are provided, if the engaged friction is less than the first engaged friction threshold value and if the current value of the kinematic quantity is less than the first kinematic quantity threshold value, preferably it is determined that the estimate of the potential friction is not available.

In a preferred embodiment, said kinematic quantity is the drift angle α of the tyre and said engaged friction μ is the lateral engaged friction $F_y/F_z$. In this preferred embodiment, the first reference curve is preferably selected so that the first kinematic quantity threshold value corresponds to a drift angle comprised between 0.5° and 1.2°. The second reference curve is preferably selected so that the second kinematic quantity threshold value corresponds to a drift angle comprised between 1.2° and 2.5°.

In a preferred embodiment, said kinematic quantity is the longitudinal slip ε of the tyre and said engaged friction μ is the longitudinal engaged friction $F_x/F_z$. In this preferred embodiment, the first reference curve is preferably selected so that the first kinematic quantity threshold value corresponds to a slip at least equal to 0.5%. More preferably, the first reference curve is selected so that the first kinematic quantity threshold value corresponds to a slip comprised between 0.5 and 0.9%. Preferably, the second reference curve is selected so that the second kinematic quantity threshold value corresponds to a slip at least equal to 0.9%. More preferably, the second reference curve is selected so that the second kinematic quantity threshold value corresponds to a slip comprised between 0.9 and 1.5%. In a preferred embodiment, the working point is determined from values of lateral engaged friction $F_y/F_z$ and drift angle α when the current lateral acceleration of the tyre is greater, in absolute value, than a predetermined lateral acceleration value, and/or the working point is determined from values of longitudinal engaged friction $F_x/F_z$ and longitudinal slip ε when the current lateral acceleration of the tyre is less, in absolute value, than a predetermined lateral acceleration value and the longitudinal acceleration of the tyre is greater, in absolute value, than a predetermined longitudinal acceleration value.

Advantageously, the tyre is made to rotate on the rolling surface in transitory rolling conditions.

In a system for controlling a vehicle that uses the system and/or method of the invention, the engaged-friction/kinematic-quantity reference curves are selected relative to a tyre or tyres of model/size with specifications suitable for the vehicle under consideration.

Preferably, the system comprises a monitoring module positioned on-board the vehicle and/or on the tyre. The monitoring module is advantageously configured to detect and process physical quantities correlated to the longitudinal and/or lateral forces exchanged in the contact plane between the tyre and the rolling surface, to the vertical load acting on the tyre, to the longitudinal slip and/or to the drift angle of the tyre.

In a preferred embodiment, the monitoring module comprises a monitoring device positioned on the tyre suitable for detecting the deformations undergone by the tyre while rolling. Preferably, the monitoring device comprises an accelerometer of the bi-axial or tri-axial type associated with the inner surface of the tyre, in a portion thereof opposite the tread.

The monitoring module can comprise a GPS receiver and/or an ABS encoder and/or a phonic wheel and/or a gyroscope.

BRIEF DESCRIPTION OF THE DRAWING

Further characteristics and advantages of the present invention will become clear from the following detailed description of some example embodiments thereof, provided just as non-limiting examples, said description being made with reference to the attached drawings, in which:

FIGS. 5-9 show results of experimental tests carried out by the Applicant to evaluate the performance of the method and system of the invention;

DETAILED DESCRIPTION OF THE INVENTION

Figure 1:
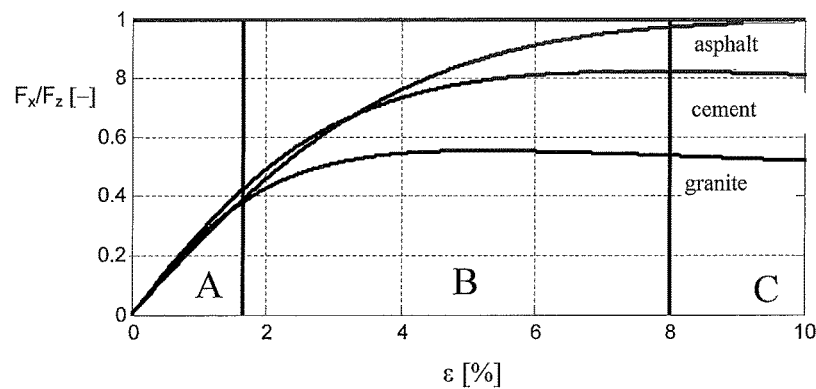
FIG. 1 schematically shows three examples of engaged friction/slip curves characteristic of three different rolling surfaces, corresponding to three different potential friction values.

In the following description, to illustrate the figures we will use identical reference numerals to indicate constructive elements with the same function.

Figure 2:
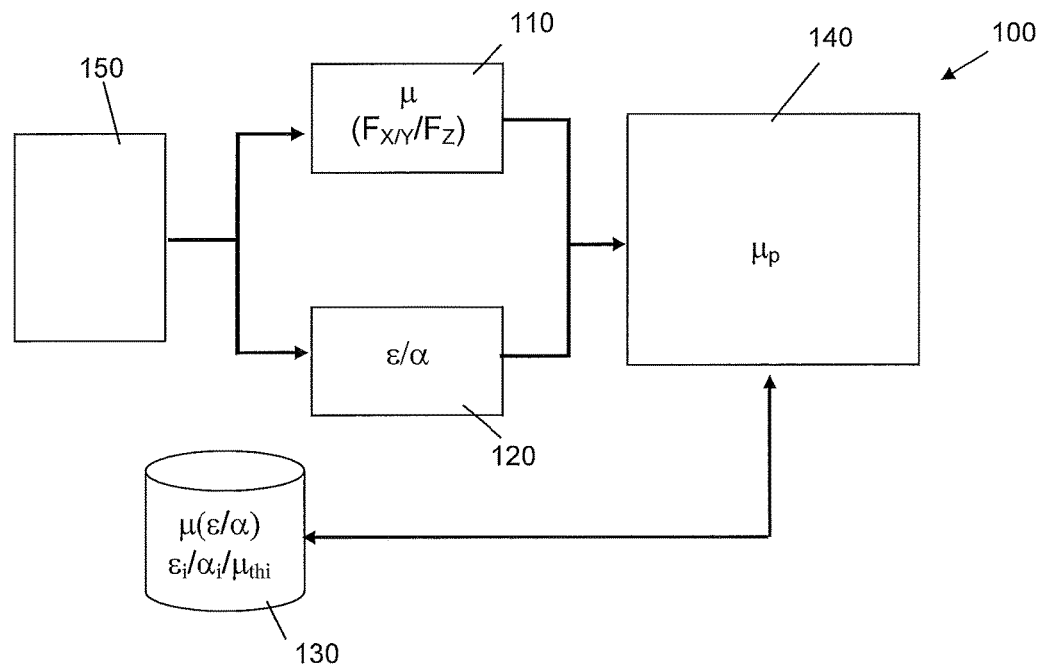
FIG. 2 schematically shows a system for estimating the potential friction according to an embodiment of the invention.

FIG. 2 shows a system, wholly indicated with 100, for estimating the potential friction between a vehicle tyre and a rolling surface.

The system 100 comprises at least one processing module configured to carry out the estimation according to the invention.

Said at least one processing module can be implemented through suitably configured hardware, software and/or firmware.

For example, the system 100 can comprise a monitoring module 150, a module 110 for estimating engaged friction $\mu$, a module 120 for estimating kinematic quantities $\epsilon/\alpha$, a memory 130 and a module 140 for estimating the potential friction $\mu_p$.

The monitoring module 150 can be positioned on-board the vehicle and/or on the tyre and is configured to detect (typically through signal acquisition) and process physical quantities correlated to the longitudinal and/or lateral forces exchanged in the contact plane between the tyre and the rolling surface, to the vertical load acting on the tyre, to the longitudinal slip and/or to the drift angle of the tyre.

The module 110 is configured to determine the longitudinal and/or lateral engaged friction $\mu$ based on the quantities detected by the monitoring module 150.

The module 120 is configured to determine the (longitudinal) slip $\epsilon$ and/or the drift angle $\alpha$ of the tyre based on the quantities detected by the monitoring module 150. The memory 130 stores predetermined engaged-friction/kinematic-quantity reference curves $\mu(\epsilon/\alpha)$ and predetermined kinematic quantity and/or engaged friction threshold values $\epsilon_i/\mu_{thi}$.

The memory 130 can also store potential friction values estimated according to the estimation method of the invention and/or kinematic quantity and/or engaged friction values determined by the modules 110 and 120.

The module 140 is configured to execute an estimation algorithm of potential friction $\mu_p$ according to the teachings of the present invention, based on the data provided by the modules 110, 120 and 130.

It should also be observed that if in the example of FIG. 2 the modules 110, 120, 130, 140, 150 are shown as distinct entities, they can form a single module or modules in a different number and/or combined in a different way from what is illustrated.

Preferably, the modules 110, 120 and 140 are configured to carry out the aforementioned determinations/estimations at predetermined times (for example at each turn of the wheel or according to a predetermined frequency).

The monitoring module 150 can comprise a monitoring device positioned on the tyre suitable for detecting the deformations undergone by the tyre while rolling (comprising, for example, an accelerometer of the bi-axial or tri-axial type associated with the inner surface of the tyre, in its portion opposite the tread) and/or a GPS receiver and/or an ABS encoder and/or a phonic wheel and/or a gyroscope.

The longitudinal and lateral forces $F_x$, $F_y$ exchanged in the contact plane between the tyre and the rolling surface and the vertical load $F_z$ acting on the tyre can, for example, be determined by using the data provided by the aforementioned monitoring device positioned on the tyre suitable for detecting the deformations undergone by the tyre.

The longitudinal slip $\epsilon$, defined by the following relationship:

$$\epsilon=(\omega R-V)/\omega R\text{(in acceleration) or } \epsilon=(\omega R-V)/V\text{(in braking)},$$

can, for example, be determined using data provided by the ABS encoder or by the phonic wheel to determine the rolling speed $\omega R$ of each tyre and data provided by the GPS receiver to determine the speed of forward motion of the vehicle V.

In turn, the drift angle $\alpha$ can, for example, be determined using data provided by a gyroscope and/or by an accelerometer.

For the sake of simplicity of explanation, hereafter reference will be made to the estimation of potential friction from data of longitudinal engaged friction (defined as the ratio between the longitudinal force $F_X$ exchanged in the contact plane between the tyre and the rolling surface and the vertical load $F_Z$ acting on the tyre) and of (longitudinal) slip $\epsilon$.

Figure 3:
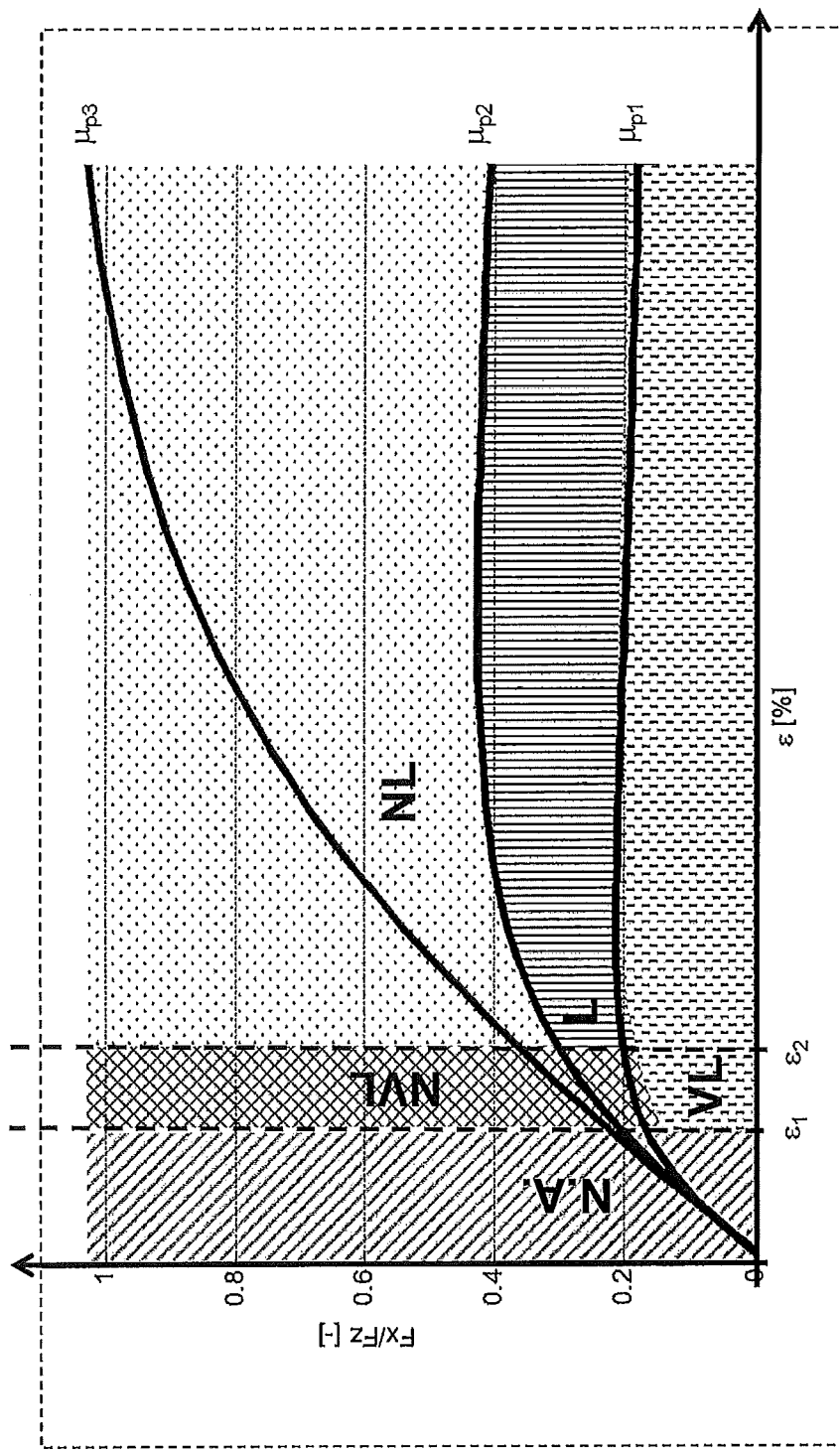
FIG. 3 shows an engaged friction/slip graph with three examples of characteristic curves of three different rolling surfaces, schematically illustrating the operation of an estimation algorithm according to an embodiment of the invention using two slip thresholds and two engaged friction/slip reference curves.
Figure 4:
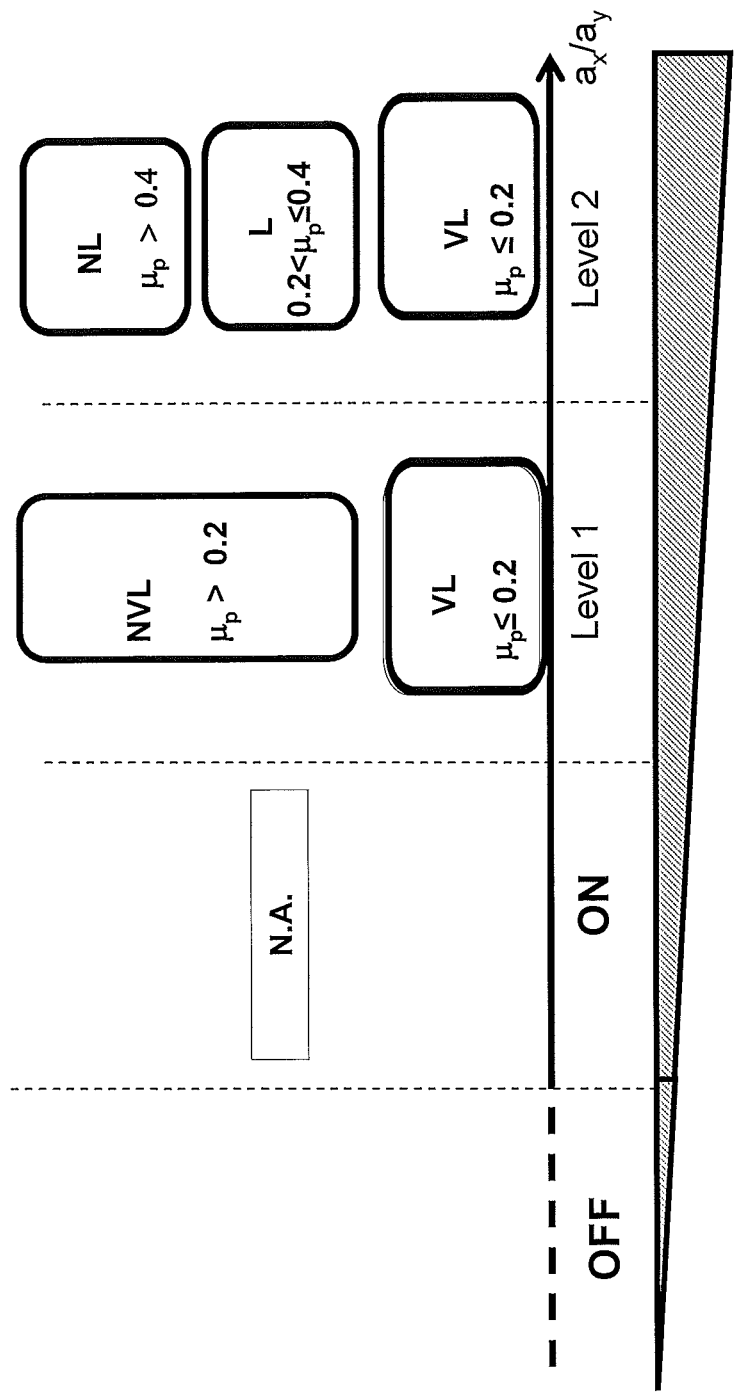
FIG. 4 schematically shows three working regions of an estimation algorithm of potential friction according to the invention as a function of the longitudinal/lateral acceleration of a vehicle.

FIGS. 3-4 schematically illustrate the operating principle of an estimation algorithm of potential friction according to an embodiment of the invention.

According to this embodiment, the algorithm comprises the following steps (carried out, for example, at each turn of the wheel or according to a predetermined frequency):

a) determining a current working point of a tyre given by values of engaged friction $F_X/F_Z$ and current slip $\epsilon$ provided by the modules 110 and 120;

b) comparing the current slip $\epsilon$ with a first threshold value $\epsilon_1$ of slip provided by the memory 130;

c) if the current slip $\epsilon$ is less than said first threshold value $\epsilon_1$, providing an output indicative of the fact that the estimation of the potential friction is not available (N.A.). Possibly, if it was possible to determine that there is a free-rolling condition, an estimation algorithm of potential friction operating in free-rolling conditions can be used;

d) if the current slip $\epsilon$ is greater than said first threshold value $\epsilon_1$, comparing the current slip $\epsilon$ also with a second threshold value $\epsilon_2$ of slip (with $\epsilon_2 > \epsilon_1$) provided by the memory 130;

e) if the current slip $\epsilon$ is comprised between said first threshold value $\epsilon_1$ and said second threshold value $\epsilon_2$ and e1) if said working point is above a first engaged friction/slip reference curve corresponding to a first reference value $\mu_{p1}$ of potential friction, excluding that the value of the potential friction is equal to or less than said first reference value $\mu_{p1}$, i.e. determining that the value of the potential friction is greater than the first reference value $\mu_{p1}$ of potential friction ($\mu_p > \mu_{p1}$) and providing in output a result indicative of potential friction "not very low" (NVL);

e2) if said working point is below or on said first reference curve, determining that the value of the potential friction is less than or equal to said first reference value $\mu_{p1}$ of potential friction ($\mu_p \leq \mu_{p1}$) and providing in output a result indicative of potential friction "very low" (VL);

f) if the current slip $\epsilon$ is greater than said second threshold value $\epsilon_2$, f1) if said working point is above a second engaged friction/slip reference curve corresponding to a second reference value $\mu_{p2}$ of potential friction (with $\mu_{p2} > \mu_{p1}$), excluding that the value of the potential friction is equal to or less than said second reference value $\mu_{p2}$, i.e. determining that the potential friction is greater than the second reference value $\mu_{p2}$ of potential friction ($\mu_p > \mu_{p2}$) and providing in output a result indicative of potential friction "not low" (NL);

f2) if said working point is comprised between said first reference curve and said second reference curve, excluding that the value of the potential friction is very low, i.e. determining that the value of the potential friction is comprised between said first reference value $\mu_{p1}$ and said second reference value $\mu_{p2}$ ($\mu_{p1} < \mu_p \leq \mu_{p2}$) and providing in output a result indicative of potential friction "low" (L);

f3) if said working point is below or on said first reference curve, determining that the value of the potential friction is less than or equal to said first reference value $\mu_{p1}$ of potential friction ($\mu_p \leq \mu_{p1}$) and providing in output a result indicative of potential friction "very low" (VL).

FIG. 3 shows: the first reference curve corresponding to the first reference value $\mu_{p1}$ of potential friction (with $\mu_{p1}$ about equal to 0.2); the second reference curve corresponding to the second reference value $\mu_{p2}$ of potential friction (with $\mu_{p2}$ about equal to 0.4); a third engaged friction $(F_X/F_Z)$/slip ($\epsilon$) curve, corresponding to a value of potential friction $\mu_{p3}$ greater than $\mu_{p2}$ (in the example, $\mu_{p3}$ about equal to 1); and the first and second slip threshold $\epsilon_1$ and $\epsilon_2$, respectively equal to 0.7% and 1.2%. The vertical lines at $\epsilon_1$ and $\epsilon_2$ divide the plane $(F_X/F_Z)/\epsilon$ into three vertical working regions: a first region with $\epsilon < \epsilon_1$ in which the engaged friction/slip curves are juxtaposed and are substantially indistinguishable; a second region with $\epsilon_1 < \epsilon < \epsilon_2$ in which the first reference curve at lower potential friction ($\mu_{p1}$ about 0.2) becomes distinguishable from the other curves above it at higher potential friction; and a third region with $\epsilon > \epsilon_2$ in which the second reference curve at potential friction $\mu_{p2}$ also becomes distinguishable from the other curves above it at higher potential friction.

The first threshold $\epsilon_1$ corresponds to a slip value in which the first reference curve corresponding to a lower potential friction $\mu_{p1}$ becomes substantially distinguishable from the other curves corresponding to higher potential frictions. In turn, the second threshold $\epsilon_2$ corresponds to a slip value in which the second reference curve corresponding to a potential friction $\mu_{p2}$ higher than $\mu_{p1}$ becomes substantially distinguishable from the third curve at potential friction $\mu_{p3}$ greater than $\mu_{p2}$. It should be observed that, once the second threshold $\epsilon_2$ has been defined, the third curve is not used by this embodiment of the estimation algorithm of the potential friction. Therefore, it is not necessary for such a curve to be stored in the memory 130.

In the first region, the estimation of potential friction according to this embodiment of the algorithm of the present description is not available (N.A.).

In the second region, the tyre-rolling surface system is in a transitory rolling condition with slip (corresponding to longitudinal acceleration values $a_x$) that is relatively low ($\epsilon_1 < \epsilon < \epsilon_2$). In this region, the algorithm is able to distinguish two areas: an area NVL with potential friction "not very low" ($\mu_p > \mu_{p1}$) and an area VL with potential friction "very low" ($\mu_p \leq \mu_{p1}$). The curves with potential friction $\mu_p > \mu_{p1}$ are still juxtaposed in this region, hence it is not possible, in this embodiment of the algorithm, to obtain further information.

In the third region, the tyre-rolling surface system is in a transitory rolling condition with slip (corresponding to longitudinal acceleration values $a_x$) that are higher ($\epsilon > \epsilon_2$). In this region, the algorithm is able to distinguish three areas: an area NL with potential friction "not low" ($\mu_p > \mu_{p2}$), an area L with potential friction "low" ($\mu_{p1} < \mu_p \leq \mu_{p2}$) and an area VL with potential friction "very low" ($\mu_p \leq \mu_{p1}$). According to a characteristic of the algorithm of the invention, the estimation of the potential friction is carried out according to a progressive logic that proceeds by successive levels of discrimination as a transitory rolling condition progresses (for example, with the increase, in absolute value, of the longitudinal acceleration value $a_x$).

In particular, with reference to FIG. 4, when passing from a free-rolling condition (for example rectilinear rolling at almost constant low speed) to a transitory rolling condition (level 1), it is possible to discriminate two areas VL and NVL of potential friction ("very low" and "not very low") to then manage (level 2), as the transitory rolling condition progresses, to discriminate three areas VL, L and NL of potential friction ("very low", "low" and "not low").

The potential friction $\mu_p$ between the tyre and the rolling surface is estimated with increasing precision as the slip values increase, but without the need to reach high slip and/or engaged friction values.

Thanks to the progressive logic it is possible to obtain useful information on the potential friction (i.e. to begin to exclude, already for relatively low acceleration/deceleration values, risky situations with very low potential friction) as soon as the available data of engaged friction and slip fall in a region in which the first reference curve with lower potential friction becomes distinguishable from the other reference curves with higher potential friction. It is then possible to obtain increasingly precise information on the potential friction as the other reference curves also become distinguishable from the respective reference curves with higher potential friction, as the current engaged friction and/or kinematic quantity values increase.

As also shown later on by the description of the experimental results, the invention makes it possible to quickly exclude the high-risk situations at relatively low slip (longitudinal acceleration) values, without the need to wait to have higher slip (longitudinal acceleration) values available to determine with increasing precision the current potential friction value.

Moreover, it makes it possible to identify rolling surfaces with medium-high potential friction at engaged friction values far from the potential friction value of the surface in question.

The possibility of distinguishing a reference curve from the others is preferably established by taking into consideration the dispersion/precision of the experimental data obtained through the monitoring module 150. The greater the precision and confidence in the experimental data, the more the slip thresholds $\epsilon_1$ and $\epsilon_2$ can be lowered and the more the difference $\Delta\mu_{p1/2}$ (with $\Delta\mu_{p1/2} = \mu_{p2} - \mu_{p1}$) in potential friction between the first and the second reference curve can be lowered. As an example, considering the sensors currently available, the reference curves can be selected so that $\Delta\mu_{p1/2}$ is equal to at least 0.15, more preferably less than 0.30 (for example equal to 0.20).

Preferably, the first reference curve, i.e. the reference curve corresponding to the lowest potential friction $\mu_{p1}$, is selected so that $\mu_{p1}$ is equal to at least 0.15; more preferably $0.15 \leq \mu_{p1} \leq 0.3$.

Preferably, the second reference curve, i.e. the reference curve corresponding to a potential friction $\mu_{p2}$ greater than $\mu_{p1}$, is selected so that $\mu_{p2}$ is equal to at least 0.35; more preferably $0.35 \leq \mu_{p2} \leq 0.50$.

Preferably, the first reference curve, i.e. the reference curve corresponding to the lowest potential friction $\mu_{p1}$, is selected so that the first threshold $\epsilon_1$ is in the range $0.5\% \leq \epsilon_1 \leq 0.9\%$.

Preferably, the second reference curve, i.e. the reference curve corresponding to the potential friction $\mu_{p2} > \mu_{p1}$, is selected so that the second threshold $\epsilon_2$ is in the range $0.9\% \leq \epsilon_2 \leq 1.5\%$, with $\epsilon_2 > \epsilon_1$.

In order to take into account the dispersion/precision of the experimental data, the engaged friction/slip reference curves are preferably considered with predetermined uncertainty bands. For example, in the case of the first reference curve with potential friction $\mu_{p1}$, all of the working points that are found below or on a reference curve with potential friction $\mu_{p1} + \Delta\mu$ (for example, with $0.05 < \Delta\mu < 0.1$), are considered as points with potential friction less than or equal to $\mu_{p1}$. The same applies for the second reference curve with potential friction $\mu_{p2}$.

It should be observed that the estimation algorithm of potential friction has been described above as an example considering two slip threshold values $\epsilon_1$ and $\epsilon_2$, two reference curves with potential friction $\mu_{p1}$ and $\mu_{p2}$ and three working regions defined by $\epsilon_1$ and $\epsilon_2$.

The algorithm of the invention can, however, be implemented considering N (with N>2) slip threshold values selected on respective N reference curves, thus defining N+1 working regions. The N slip threshold values respectively correspond to slip values in which the respective N reference curves become substantially distinguishable from reference curves with higher potential friction. In the memory 130 the N reference curves and the N slip threshold values will preferably be stored. Once the threshold $\epsilon_N$ has been defined, corresponding to a slip value at which the reference curve N with potential friction $\mu_{pN}$ becomes substantially distinguishable from a reference curve N+1 with potential friction $\mu_{pN+1} > \mu_{pN}$, it is not necessary to also store the curve N+1 in the memory 130. In each region defined by the thresholds $\epsilon_i - \epsilon_{i+1}$ (with $1 \leq i < N$), the algorithm will be able to discriminate i+1 areas of potential friction values defined by i reference curves that in such a region are distinguishable from reference curves with higher potential friction. As N increases, the algorithm will thus be able, for increasing slip values $\epsilon$, to distinguish an ever increasing number of areas of potential friction.

For example, in the case of a third slip threshold $\epsilon_3$, corresponding to a slip value in which a respective third reference curve with potential friction $\mu_{p3} > \mu_{p2}$ becomes substantially distinguishable from reference curves with higher potential friction, the third reference curve can be preferably selected so that $\mu_{p3} \geq 0.55$, more preferably $0.55 \leq \mu_{p2} \leq 0.8$, and/or so that $1.5\% \leq \epsilon_3 \leq 2.5\%$.

In general, when there are more than two thresholds/curves, such curves are selected so that the slip threshold with the highest value is preferably less than or equal to about 5%.

It should also be observed that although the estimation algorithm of potential friction is described in detail in the present description with reference to the engaged friction $F_X/F_Z$ and (longitudinal) slip $\epsilon$, the algorithm of the invention applies in a totally analogous way also to the case in which the estimation of potential friction is carried out from data of lateral engaged friction (defined as the ratio between the longitudinal force $F_Y$ exchanged in the contact plane between the tyre and the rolling surface and the vertical load $F_Z$ acting on the tyre) and of drift angle $\alpha$.

In this case, the first reference curve, i.e. the reference curve corresponding to the lowest potential friction is preferably selected so that the first threshold $\alpha_1$ is in the range $0.5° \leq \alpha_1 \leq 1.2°$.

Preferably, the second reference curve, i.e. the reference curve corresponding to the potential friction $\mu_{p2} > \mu_{p1}$, is selected so that the second threshold $\alpha_2$ is in the range $1.2° \leq \alpha_2 \leq 2.5°$, with $\alpha_2 > \alpha_1$.

In a preferred embodiment, the estimation algorithm of potential friction is configured so as to establish whether to determine the potential friction from data of lateral engaged friction and drift angle $\alpha$ and/or from data of longitudinal engaged friction and slip $\epsilon$, as a function of predetermined conditions of the tyre-rolling surface system.

For example, the estimation algorithm of potential friction can be configured to use data of lateral engaged friction and drift angle $\alpha$, when the lateral acceleration of the tyre is greater, in absolute value, than a predetermined lateral acceleration value (for example 1 m/s$^2$), or data of longitudinal engaged friction and (longitudinal) slip $\epsilon$ when the lateral acceleration of the tyre is less, in absolute value, than said predetermined lateral acceleration value (for example 1 m/s$^2$) and the longitudinal acceleration of the tyre is greater, in absolute value, than a predetermined longitudinal acceleration value (for example 0.2 m/s$^2$).

In order to evaluate the performance of the invention, the Applicant carried out experimental tests in which potential friction values were estimated using an estimation algorithm according to an embodiment of the invention of the type illustrated in FIG. 3 with two slip thresholds ($\epsilon_1 = 0.7\%$, $\epsilon_2 = 1.2\%$) and two reference curves ($\mu_{p1}$ about equal to 0.2, $\mu_{p2}$ about equal to 0.4).

The tests were carried out with Pirelli PZero™ tyres mounted on a Volvo S60 vehicle travelling on different rolling surfaces.

FIG. 5 shows the results obtained on a rolling surface of wet granite with potential friction $\mu_p$ measured equal to about 0.2, for the front right wheel, in longitudinal dynamic (engaged friction and longitudinal slip, with slip data obtained through phonic wheel), for rectilinear rolling and vehicle in acceleration from a speed of 20 km/h, with maximum acceleration of 1 m/s$^2$.

The results are provided in terms of wheel revolutions and percentage of wheel revolutions with respect to the total of the wheel revolutions carried out.

As can be seen, in the tested conditions, the system was in a substantial free-rolling region ($\epsilon < 0.7\%$) for 32% of the wheel revolutions, in a low slip region ($0.7\% \leq \epsilon < 1.2\%$) for 35% of the wheel revolutions and in a higher slip region ($\epsilon \geq 1.2\%$) for 33% of the wheel revolutions. Therefore, the algorithm was able to provide an estimate result for 68% of the wheel revolutions carried out.

In the low slip region ($0.7\% \leq \epsilon < 1.2\%$), the algorithm provided a correct result (VL, potential friction $\mu_p \leq 0.2$ "very low") in 390 revolutions out of the 391 carried out in such a region (99.74%). In the high slip region ($\epsilon \geq 1.2\%$), the algorithm provided a correct result in 347 revolutions out of the 365 carried out in such a region (95.07%). The 18 errors made in this last region occurred for estimation of "low" potential friction value (L, $0.2 < \mu_p \leq 0.4$). On the other hand, the algorithm did not provide any estimation of "not low" potential friction value (NL, $\mu_p > 0.4$).

FIG. 6a shows the results obtained in analogous conditions to the tests that gave the results shown in FIG. 5, except for the fact that the tests were carried out on a rolling surface of dry cement with potential friction $\mu_p = 0.85$ and maximum acceleration of 3 m/s$^2$.

As can be seen, in the conditions tested, the system was in a condition of substantial free-rolling ($\epsilon < 0.7\%$) for 28% of the wheel revolutions, in a low slip region ($0.7\% \leq \epsilon < 1.2\%$) for 67% of the wheel revolutions and in a higher slip region ($\epsilon \geq 1.2\%$) for 5% of the wheel revolutions. Therefore, the algorithm was able to provide an estimation result for 72% of the wheel revolutions carried out. In the low slip region ($0.7\% \leq \epsilon < 1.2\%$), the algorithm provided a correct result (NVL, potential friction $\mu_p > 0.2$ "not very low") in 714 revolutions out of 719 carried out in such a region (99.30%). In the high slip region ($\epsilon \geq 1.2\%$), the algorithm provided a correct result (NL, potential friction $\mu_p > 0.4$ "not low") in 52 revolutions out of 52 carried out in such a region (100.00%).

FIG. 6b shows the results obtained in the same conditions of the tests that led to the results shown in FIG. 6a except for the fact that the slip data was obtained, instead of with the phonic wheel, through a monitoring device positioned on the inner surface of the tyre in the portion opposite the tread and equipped with a tri-axial accelerometer to detect the deformations undergone by the tyre while rolling. In this last case, in the low slip region ($0.7\% \leq \epsilon < 1.2\%$), the algorithm provided a correct result (NVL, potential friction $\mu_p > 0.2$ "not very low") in 716 revolutions out of 719 carried out in such a region (99.58%). The remaining data is analogous to that shown in FIG. 6a.

FIGS. 7a-7d show results of tests of the estimation algorithm according to the invention with respect to the activation of an ABS system.

The tests were carried out with Pirelli PZero™ tyres mounted on a Volvo S60 vehicle.

Figures 7A, 7B, 7C, 7D:
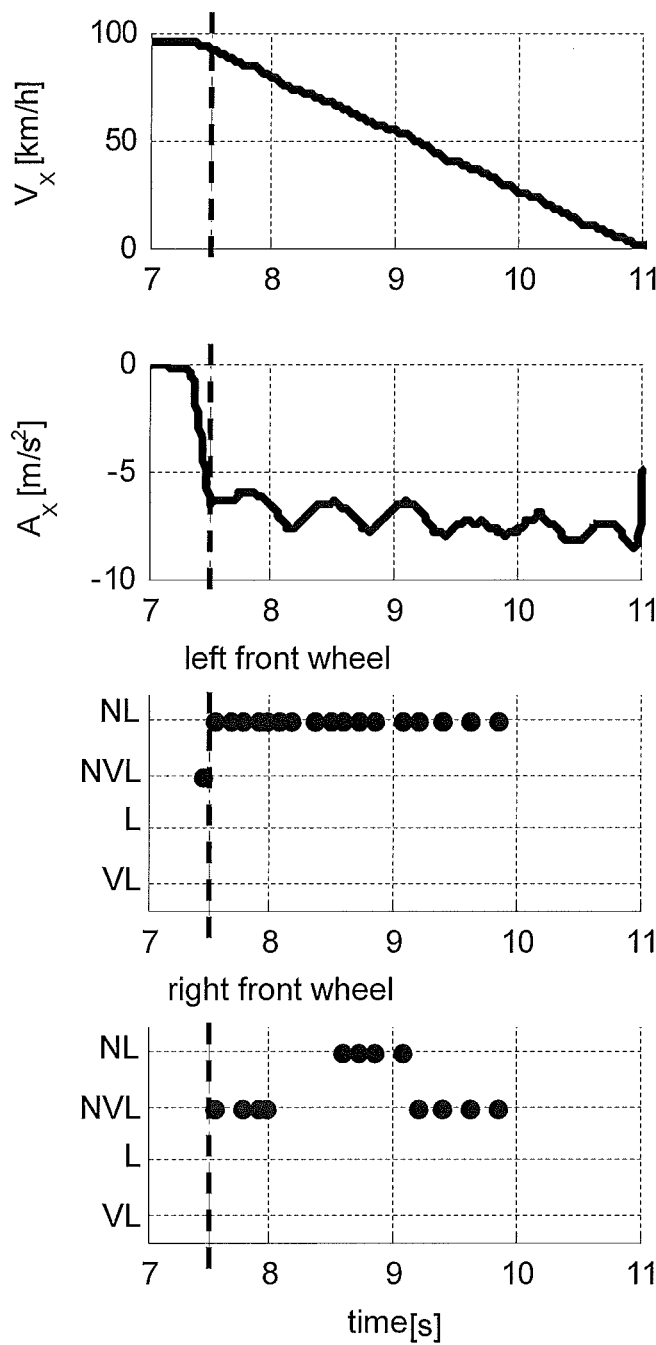

In particular, FIG. 7a shows the progress of the speed of the vehicle during a certain number of seconds of manoeuvring (indicated in abscissa) in rectilinear rolling conditions on a high grip surface, dry asphalt, $\mu_p$ about equal to 1; FIG. 7b shows the corresponding acceleration value; FIGS. 7c and 7d show the levels of potential friction estimated by the estimation algorithm according to the invention, respectively for the left front wheel and for the right front wheel of the vehicle. The dashed vertical line at about 7.5 seconds represents in the figures the moment of activation of the ABS. As can be seen, the estimation algorithm according to the invention is able to provide a first estimated value of potential friction ($\mu_p > 0.2$, "not very low", NVL) before the intervention of the ABS.

In an ABS system that operates by different intervention logics according to whether the vehicle is in a condition of low or high potential friction, such information can be very useful to allow the system to know in advance (possibly even before its actual activation) which of the two logics to adopt.

Figure 8:
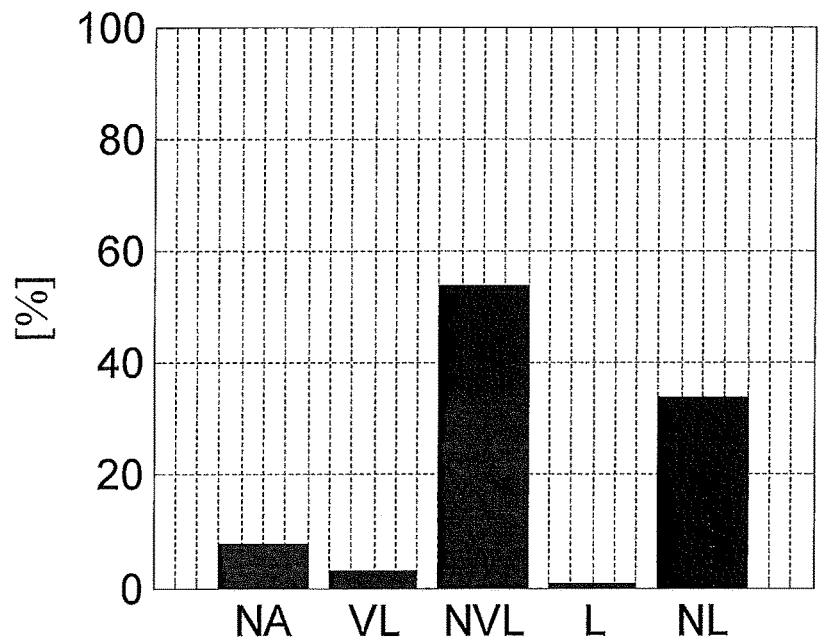

FIG. 8 shows the estimation results of potential friction obtained with Pirelli PZero™ tyres mounted on a Volvo S60 vehicle on dry asphalt ($\mu_p$ equal to about 1) through an estimation algorithm according to an embodiment of the invention of the type illustrated in FIG. 3, for a vehicle in longitudinal dynamic, with two slip thresholds ($\epsilon_1 = 0.7\%$, $\epsilon_2 = 1.2\%$) and two reference curves ($\mu_{p1}$ about equal to 0.2, $\mu_{p2}$ about equal to 0.4).

Figure 9:
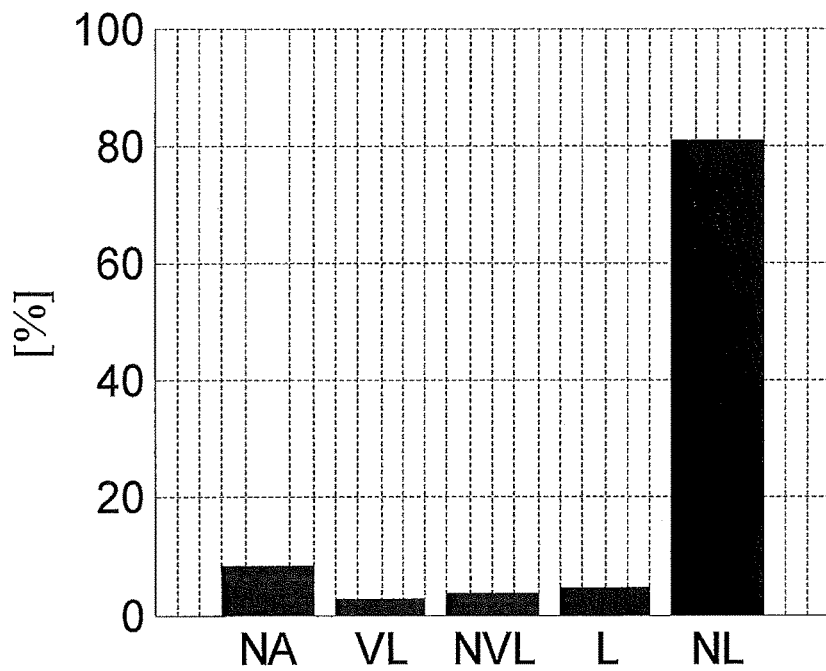

FIG. 9 shows similar results obtained with a lateral dynamic, two drift angle thresholds ($\alpha_1 = 1°$, $\alpha_2 = 2°$) and two reference curves (($\mu_{p1}$ about equal to 0.2, $\mu_{p2}$ about equal to 0.4).

In FIGS. 8 and 9, the abbreviations NA, VL, NVL, L, NL respectively indicate estimation results that are not available, very low ($\mu_p \leq 0.2$), not very low ($\mu_p > 0.2$), low ($0.2 < \mu_p \leq 0.4$), not low ($\mu_p > 0.4$).

The results expected for the considered dry asphalt surface ($\mu_{p1}$ about equal to 1) were NVL ($\mu_p > 0.2$) for relatively low acceleration values within the region $\epsilon_1 \leq \epsilon < \epsilon_2$ or $\alpha_1 \leq \alpha < \alpha_2$ and NL ($\mu_p > 0.4$) for higher acceleration values in the region $\epsilon > \epsilon_2$ or $\alpha > \alpha_2$.

In FIG. 8 the percentage of correct results (NVL and NL) obtained according to the progressive logic forming the basis of the estimation algorithm according to the invention reaches in total 85%. In FIG. 9, 80% of the results are located in the area of potential friction NL ($\mu_p > 0.4$).

The percentages of results not available are in any case less than 10%.

Table 1 below shows the longitudinal acceleration/deceleration values and engaged friction/potential friction ratios $\mu_p$ necessary to reach the slip thresholds $\epsilon_1 = 0.7\%$ and $\epsilon_2 = 1.2\%$ for different rolling surfaces with Pirelli PZero™ tyres mounted on a Volvo S60 vehicle.

TABLE 1

| | | accel./decel [m/s²]/(engaged friction/$\mu_p$) [%] | | | |
|---|---|---|---|---|---|
| Rolling surface | Potential friction $\mu_p$ | 1ª threshold $\epsilon_1 = 0.7\%$ | | 2ª threshold $\epsilon_2 = 1.2\%$ | |
| | | accel. | decel. | accel. | decel. |
| dry asphalt | Not low 1 | 1.5/25 | 3/25 | 3/40 | 6/40 |
| dry cement | Not low 0.8 | 1.4/35 | 2.8/35 | 2.5/60 | 5/60 |
| dry granite | Low 0.4 | 1.2/45 | 2.5/45 | 2/75 | 4/75 |
| wet granite | Very low 0.2 | 0.35/50 | 0.7/50 | 0.55/80 | 1.1/80 |

As can be seen, the acceleration/deceleration values required to reach the first threshold $\epsilon_1$ and activate the estimation algorithm according to the invention, are relatively low. Let us consider, for example, that in an urban journey a longitudinal acceleration of 0.7 m/s² can be exceeded 30% of the time. Standard braking, moreover, typically involves a deceleration of about 2-3 m/s².

It can also be observed that the percentages obtained of engaged friction/potential friction when the threshold $\epsilon_1$ is reached are in any case less than 50%. This means that the estimation algorithm according to the invention always activated well before the potential friction value of the surface in question was reached. In addition, the percentages obtained of engaged friction/potential friction when the threshold $\epsilon_2$ was reached are comprised between 40-80%. The estimation algorithm according to the invention therefore managed to reach the high slip region, in which it is able to distinguish three areas of potential friction, much before the potential friction value of the surface in question was reached. Table 2 below shows results similar to those of Table 1, except for the fact that it considers a lateral dynamic (lateral engaged friction $F_y/F_z$ and drift angle $\alpha$), drift angle thresholds $\alpha_1 = 1°$ and $\alpha_2 = 2°$, three rolling surfaces and lateral acceleration values.

TABLE 2

| | | accel. [m/s²]/(engaged friction/$\mu_p$) [%] | |
|---|---|---|---|
| Rolling surface | Potential friction $\mu_p$ | 1ª threshold $\alpha_1 = 1°$ | 2ª threshold $\alpha_2 = 2°$ |
| dry asphalt | Not low 1 | 3/30 | 4/40 |
| dry cement | Not low 0.8 | 2.5/35 | 3.5/45 |
| wet asphalt | low 0.4 | 2/50 | 3/70 |

It should be observed that the estimation algorithm of potential friction was described above as an example considering slip thresholds $\epsilon_i$.

However, the algorithm of the invention can be implemented in a totally analogous way considering engaged friction thresholds instead of the aforementioned slip thresholds.

Figure 10:
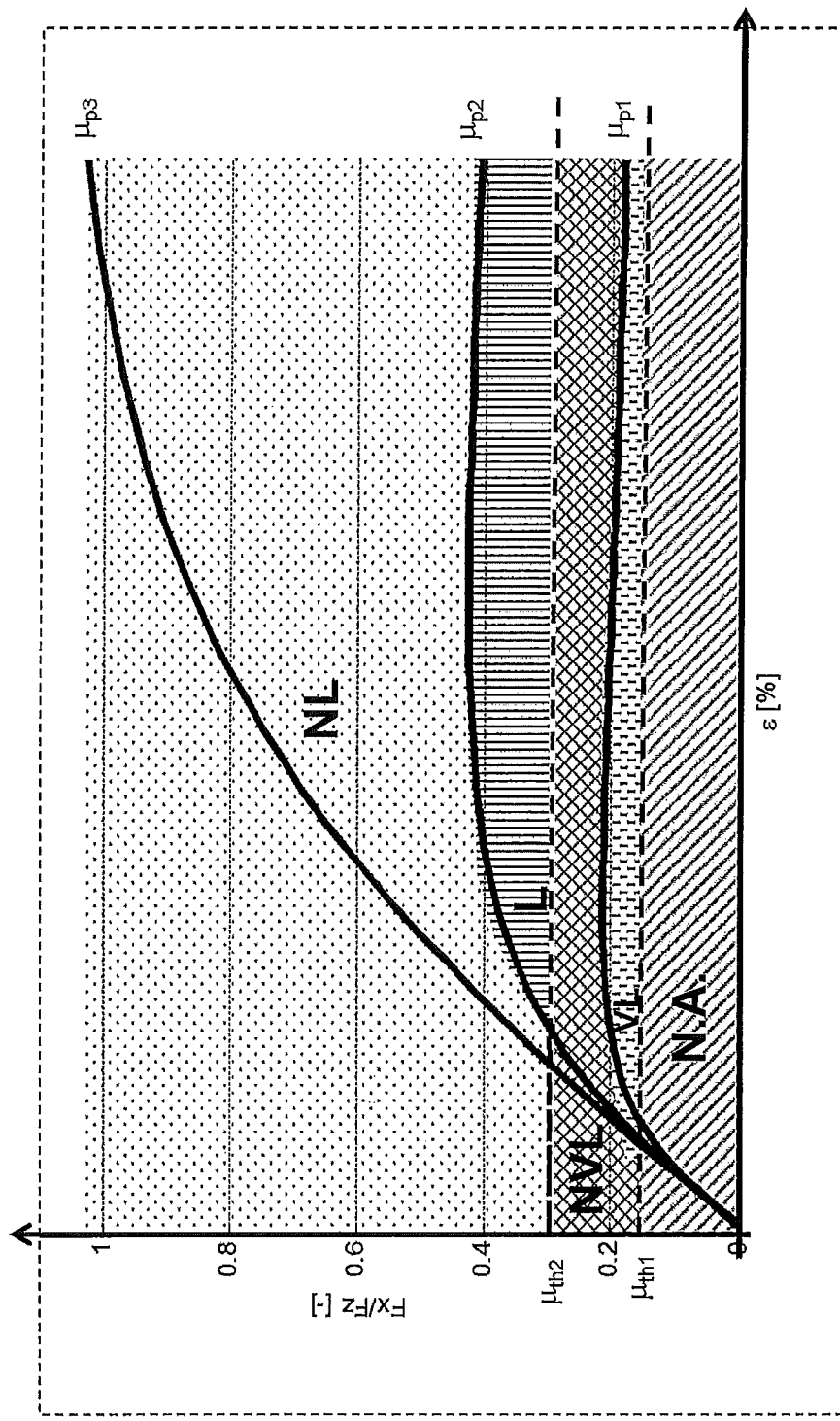
FIG. 10 shows an engaged friction/slip graph with three examples of characteristic curves of three different rolling surfaces, schematically illustrating the operation of an estimation algorithm according to an embodiment of the invention using two engaged friction thresholds and two engaged friction/slip reference curves.

An embodiment of this type of implementation is schematically illustrated in FIG. 10 showing a first reference curve corresponding to a first reference value $\mu_{p1}$ of potential friction (with $\mu_{p1}$ about equal to 0.2); a second reference curve corresponding to a second reference value $\mu_{p2}$ of potential friction (with $\mu_{p2}$ about equal to 0.4); a third reference curve corresponding to a third reference value $\mu_{p3}$ of potential friction with $\mu_{p3} > \mu_{p2}$ (in the example $\mu_{p3}$ about equal to 1); and a first and a second threshold of engaged friction $\mu_{th1}$ and $\mu_{th2}$, with $\mu_{th2} > \mu_{p1} > \mu_{th1}$. Similarly to what is described above with reference to the slip thresholds, the first threshold $\mu_{th1}$ corresponds to a value of engaged friction in which the first reference curve corresponding to a lower potential friction $\mu_{p1}$ becomes substantially distinguishable from the other curves corresponding to higher potential frictions $\mu_{p2}$, $\mu_{p3}$. In turn, the second threshold $\mu_{th2}$ corresponds to a value of engaged friction in which the second reference curve at potential friction $\mu_{p2}$ greater than $\mu_{p1}$ becomes substantially distinguishable from the third reference curve corresponding to higher potential friction $\mu_{p3}$.

Preferably, the first reference curve is selected so that $\mu_{p1}$ is equal to at least 0.15; more preferably $0.15 \leq \mu_{p1} \leq 0.3$.

Preferably, the second reference curve is selected so that $\mu_{p2}$ is equal to at least 0.35; more preferably $0.35 \leq \mu_{p2} \leq 0.50$.

Preferably, the first reference curve is selected so that the first threshold $\mu_{th1}$ is within the range $0.05 \leq \mu_{th1} \leq 0.20$ (in the example, $\mu_{th1} = 0.15$).

Preferably, the second reference curve is selected so that Ia second threshold $\mu_{th2}$ is in the range $0.25 \leq \mu_{th2} \leq 0.40$ (in the example, $\mu_{th2} = 0.3$).

According to the embodiment of FIG. 10, the algorithm comprises the following steps (carried out, for example, at every wheel revolution or according to a predetermined frequency):

a) determining a current working point of a tyre given by values of engaged friction $F_x/F_z$ and current slip $\epsilon$ provided by the modules 110 and 120;

b) comparing the engaged friction $F_x/F_z$ with the first threshold value $\mu_{th1}$ of engaged friction provided by the memory 130;

c) if the engaged friction $F_x/F_z$ is less than said first threshold value $\mu_{th1}$, providing an output indicative of the fact that the estimation of the potential friction is not available (N.A.);

d) if the engaged friction $F_x/F_z$ is greater than said first threshold value $\mu_{th1}$, comparing the engaged friction $F_x/F_z$ also with the second threshold value $\mu_{th2}$ provided by the memory 130;

e) if the engaged friction $F_x/F_z$ is comprised between said first threshold value $\mu_{th1}$ and said second threshold value $\mu_{th2}$ and e1) if said working point is above the first engaged friction/slip reference curve corresponding to the first reference value $\mu_{p1}$ of potential friction, excluding that the value of the potential friction is equal to or less than said first reference value $\mu_{p1}$, i.e. determining that the value of the potential friction is greater than the first reference value $\mu_{p1}$ of potential friction and providing in output a result indicative of potential friction "not very low" (NVL, $\mu_p > \mu_{p1}$);

e2) if said working point is below or on said first reference curve, determining that the value of the potential friction is less than or equal to said first reference value $\mu_1$ of potential friction and providing in output a result indicative of potential friction "very low" (VL, $\mu_p \leq \mu_{p1}$);

f) if the engaged friction $F_X/F_Z$ is greater than said second threshold value $\mu_{th2}$;

f1) if said working point is above the second engaged friction/slip reference curve corresponding to the second reference value $\mu_{p2}$ of potential friction, excluding that the value of the potential friction is equal to or less than said second reference value $\mu_{p2}$, i.e. determining that the potential friction is greater than the second reference value $\mu_{p2}$ of potential friction and providing in output a result indicative of potential friction "not low" (NL, $\mu_p > \mu_{p2}$);

f2) if said working point is comprised between said first reference curve and said second reference curve (i.e. it is below or on the second reference curve), excluding that the value of the potential friction is very low, i.e. determining that the value of the potential friction is comprised between said first reference value $\mu_{p1}$ and said second reference value $\mu_{p2}$ and providing in output a result indicative of potential friction "low" (L, $\mu_{p1} < \mu_p \leq \mu_{p2}$).

It should be observed that the estimation algorithm of potential friction was described above as an example considering either slip thresholds $\epsilon_i$ or engaged friction thresholds $\mu_i$.

The use of one or other type of threshold can be established, for example, based on the precision and/or confidence in the experimental data and/or on predetermined performance requirements. For example, in the case of greater precision/confidence in the data of engaged friction, it may be preferred to use engaged friction thresholds. On the other hand, in the case of greater precision/confidence in the data of slip, it may be preferred to use slip thresholds. Moreover, in applications in which it is required to more quickly discriminate (i.e. at low slip values) low values of potential friction, it may be preferred to use slip thresholds. On the other hand, in applications in which it is required to more quickly discriminate high values of potential friction, it may be preferred to use engaged friction thresholds.

It should also be observed that, according to a preferred embodiment, the algorithm of the invention can be implemented in a totally analogous way to what has been described above with reference to FIGS. 3 and 10 but considering both engaged friction thresholds and slip (or drift) thresholds.

Figure 11:
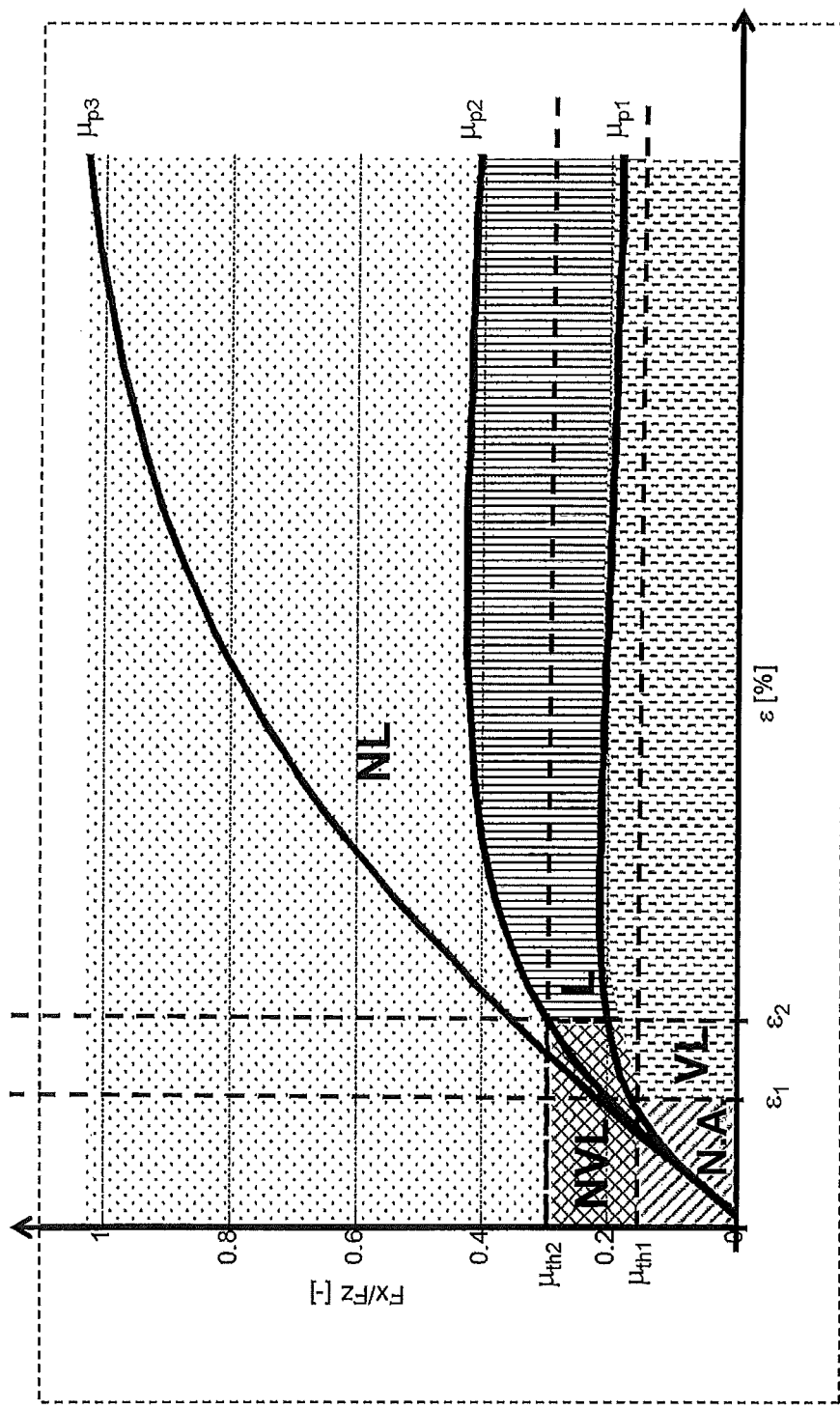
FIG. 11 shows an engaged friction/slip graph with three examples of characteristic curves of three different rolling surfaces, schematically illustrating the operation of an estimation algorithm according to an embodiment of the invention using both two slip thresholds and two engaged friction thresholds and two engaged friction/slip reference curves.

An example of this type of implementation is schematically illustrated in FIG. 11 where, in addition to the reference curves and to the potential friction thresholds $\mu_{th1}$ and $\mu_{th2}$ of FIG. 10, slip thresholds $\epsilon_1$ and $\epsilon_2$ analogous to those shown in FIG. 3 are shown.

According to the embodiment of FIG. 11, the algorithm—comparing the working points determined with the potential friction thresholds $\mu_{th1}$ and $\mu_{th2}$ and the slip thresholds $\epsilon_1$ and $\epsilon_2$—is able to identify five areas of potential friction: the area N.A. ("not available"), defined by $\mu < \mu_{th1}$ and $\epsilon < \epsilon_1$, in which the algorithm is unable to provide the estimation of potential friction; an area NVL, defined by $\mu_{th1} < \mu < \mu_{th2}$, $\epsilon < \epsilon_2$ and working points above the first reference curve, in which the algorithm provides an estimation of potential friction "not very low" ($\mu_p > \mu_{p1}$); an area VL, defined by $\epsilon > \epsilon_1$ and working points on or below the first reference curve, in which the algorithm provides an estimation of potential friction "very low" ($\mu_p \leq \mu_{p1}$); an area L, defined by $\epsilon > \epsilon_2$ and working points comprised between the first and the second reference curve, in which the algorithm provides an estimation of potential friction "low" ($\mu_{p1} < \mu_p \leq \mu_{p2}$); an area NL, defined by $\mu > \mu_{th2}$ and working points above the second reference curve, in which the algorithm provides an estimation of potential friction "not low" $\mu_p > \mu_{p2}$).

In particular, the algorithm will comprise the following steps (carried out, for example, at each wheel revolution or according to a predetermined frequency):

1) determining a current working point of a tyre given by values of engaged friction $F_X/F_Z$ and current slip $\epsilon$ provided by the modules 110 and 120;

2) comparing the current slip $\epsilon$ with the first threshold value $\epsilon_1$ of slip and the engaged friction $F_X/F_Z$ with the first threshold value $\mu_{th1}$ of engaged friction;

3) if both the current slip $\epsilon$ and the engaged friction $F_X/F_Z$ are below the respective first threshold values $\epsilon_1$ and $\mu_{th1}$, providing an output indicative of the fact that the estimation of the potential friction is not available (N.A.) and/or referring to an estimation algorithm of potential friction operating in free-rolling conditions;

4) if just the current slip $\epsilon$ is less than the first threshold value $\epsilon_1$:
   if the engaged friction $F_X/F_Z$ is comprised between the first and the second engaged friction threshold value $\mu_{th1}$ and $\mu_{th2}$, determining that the value of the potential friction is greater than the first reference value $\mu_{p1}$ of potential friction and providing in output a result indicative of potential friction "not very low" (NVL, $\mu_p > \mu_{p1}$);
   if the engaged friction $F_X/F_Z$ is greater than the second engaged friction threshold value $\mu_{th2}$, determining that the value of the potential friction is greater than the second reference value $\mu_{p2}$ of potential friction and providing in output a result indicative of potential friction "not low" (NL, $\mu_p > \mu_{p2}$);

5) if the current slip $\epsilon$ is comprised between the first and the second threshold value $\epsilon_1$ and $\epsilon_2$:
   if the working point is above the first engaged friction/slip reference curve and if the engaged friction $F_X/F_Z$ is comprised between the first and the second engaged friction threshold value $\mu_{th1}$ and $\mu_{th2}$, determining that the value of the potential friction is greater than the first reference value $\mu_{p1}$ of potential friction and providing in output a result indicative of potential friction "not very low" (NVL, $\mu_p > \mu_{p1}$);
   if the working point is above the first engaged friction/slip reference curve and if the engaged friction $F_X/F_Z$ is greater than the second engaged friction threshold value $\mu_{th2}$, determining that the value of the potential friction is greater than the second reference value $\mu_{p2}$ of potential friction and providing in output a result indicative of potential friction "not low" (NL, $\mu_p > \mu_{p2}$);
   if the working point is below or on said first reference curve, determining that the value of the potential friction is less than or equal to said first reference value $\mu_1$ of potential friction and providing in output a result indicative of potential friction "very low" (VL, $\mu_p \leq \mu_{p1}$)

6) if the current slip $\epsilon$ is greater than the second threshold value $\epsilon_2$, proceeding as described in points f1)-f3) with reference to FIGS. 3-4.

Similarly, instead of proceeding according to points 4)-6), the estimation algorithm can proceed, after point 3), as follows:

4') 'if the engaged friction $F_X/F_Z$ is less than the first threshold value $\mu_{th1}$:
   if the current slip $\epsilon$ is greater than the first threshold value of slip $\epsilon_1$, determining that the value of the potential friction is less than or equal to said first reference value $\mu_{p1}$ of potential friction and providing in output a result indicative of potential friction "very low" (VL, $\mu_p \leq \mu_{p1}$);

5') 'if the engaged friction $F_X/F_Z$ is comprised between the first and the second threshold value $\mu_{th1}$ and $\mu_{th2}$:

if the working point is below or on said first reference curve, determining that the value of the potential friction is less than or equal to said first reference value $\mu_{p1}$ of potential friction and providing in output a result indicative of potential friction "very low" (VL, $\mu_p \leq \mu_{p1}$);

if the current slip $\epsilon$ is less than the second threshold value of slip $\epsilon_2$ and if the working point is above the first engaged friction/slip reference curve, determining that the value of the potential friction is greater than the first reference value $\mu_{p1}$ of potential friction and providing in output a result indicative of potential friction "not very low" (NVL, $\mu_p > \mu_{p1}$);

if the current slip $\epsilon$ is greater than the second threshold value of slip $\epsilon_2$ and if the working point is above the first engaged friction/slip reference curve, determining that the value of the potential friction is comprised between said first reference value $\mu_{p1}$ and said second reference value $\mu_{p2}$ and providing in output a result indicative of potential friction "low" (L, $\mu_{p1} < \mu_p \leq \mu_{p2}$), 6') 'if the engaged friction $F_X/F_Z$ is greater than the second threshold value $\mu_{th2}$, proceeding as described in points f1)-f2) with reference to FIG. 10.

As can be seen from a comparison between the areas discriminated in the examples of FIGS. 3 and 10 and those discriminated in the example of FIG. 11, the use of both the slip thresholds and the engaged friction thresholds makes it possible to estimate the potential friction in a more detailed manner.

Moreover, considering that the friction curves relative to real surfaces can differ from those represented by the numerical reference curves (derivable and represented/defined in the memory 130 through known models), the Applicant considers that the combined use of slip thresholds and engaged friction thresholds ensures that more precise estimates of potential friction are obtained.

As already stated above with reference to the embodiment of FIG. 3, it should be observed that, although the estimation algorithm of potential friction of the embodiments of FIGS. 10 and 11 has been described in detail with reference to the engaged friction $F_x/F_z$ and (longitudinal) slip $\epsilon$, the estimation method of the invention applies in a totally analogous way also to the case in which the estimation of potential friction is carried out from data of lateral engaged friction $F_y/F_z$ and of drift angle $\alpha$.

The invention, in its various embodiments, making it possible to carry out an estimation in real time of the potential friction of a tyre-rolling surface system, can be very useful in active controls systems of the dynamics of a vehicle and for Advanced Driver Assistance Systems (ADAS), such as Adaptive Cruise Control Systems, Collision Avoidance Systems, Pre-Crash Systems, Antilock Braking Systems (ABS) and similar.

For example, as already stated above, in an ABS system that operates by different intervention logics according to whether the vehicle is in a condition of low or high potential friction, the estimation algorithm according to the invention can be very important to allow the ABS system to know which of the two logics to adopt in advance, possibly even before its activation.

Moreover, in the case of systems for estimating and controlling the safety distance or indicating slippery conditions, the estimation algorithm according to the invention can be very useful to allow such systems to work with estimates in real time of the potential friction, avoiding giving false alarms, which are bothersome for the user, or even worse, failing to signal the user of possible dangerous situations.

The estimation algorithm according to the invention can also be used together with other technologies in order to obtain improved performance. For example, it can be used together with technologies for determining the potential friction in free-rolling conditions and/or with technologies capable of recognising the conditions of the tyre-rolling surface system (for example the roughness of the rolling surface) and their changes. In this last case, the use of crossed logics can advantageously make it possible to exploit data of potential friction estimated with the estimation method of the invention even when the vehicle is no longer travelling in transitory rolling conditions, so long as the conditions of the tyre-rolling surface system remain substantially unchanged.

The invention claimed is:

1. A method of enhancing driving control of a motor vehicle comprising a tyre based on a condition between the tyre and a rolling surface performed by the vehicle during operation of the vehicle, comprising:

storing, in an electronic memory within the vehicle, a first and a second predetermined engaged-friction/kinematic-quantity reference curve, respectively corresponding to a first and to a second reference value $\mu_{p1}$, $\mu_{p2}$ of potential friction between the tyre and the rolling surface with $\mu_{p2} > \mu_{p1}$;

storing, in the electronic memory, a first and a second predetermined kinematic quantity threshold value, or a first and a second predetermined engaged friction threshold value, said first threshold value corresponding to a kinematic quantity value or, respectively, engaged friction value where said first reference curve is substantially distinguishable from said second reference curve, and said second threshold value corresponding to a kinematic quantity value or, respectively, engaged friction value where said second reference curve is substantially distinguishable from at least one third reference curve corresponding to a third reference value $\mu_{p3}$ of potential friction with $\mu_{p3} > \mu_{p2}$;

rolling the tyre on the rolling surface to cause exchange of longitudinal and lateral forces in a plane of contact between the tyre and the surface;

detecting with monitoring equipment within the vehicle, comprising an accelerometer positioned on an inner surface of the tyre, physical quantities in the tyre rolling along said rolling surface, the physical quantities being correlated to at least one of the longitudinal and lateral forces exchanged in the contact plane between the tyre and the rolling surface, vertical load acting on the tyre, longitudinal slip of the tyre, and drift angle of the tyre;

performing with at least one processor within the vehicle the following operations:

determining engaged friction $\mu$ between the tyre and the rolling surface based on the physical quantities detected by the monitoring equipment;

determining a current value of a kinematic quantity between the tyre and the rolling surface based on the physical quantities detected by the monitoring equipment;

determining a current working point given by the engaged friction $\mu$ and the current value of the kinematic quantity;

comparing the current value of the kinematic quantity with the first and the second kinematic quantity threshold value or, respectively, the engaged friction $\mu$ with the first and the second engaged friction threshold value; and estimating the potential friction between the tyre and the rolling surface, wherein:

if the current value of the kinematic quantity or the engaged friction $\mu$ is between the respective first and second threshold value and said working point is above said first reference curve, determining that a value of the potential friction is greater than said first reference value $\mu_{p1}$;

if the current value of the kinematic quantity or the engaged friction $\mu$ is greater than the respective second threshold value and said working point is above said second reference curve, determining that the value of the potential friction is greater than said second reference value $\mu_{p2}$ of potential friction;

if the current value of the kinematic quantity or the engaged friction $\mu$ is greater than the respective second threshold value and said working point is between said first and said second reference curve, determining that the value of the potential friction is between said first reference value $\mu_{p1}$ of potential friction and said second reference value $\mu_{p2}$ of potential friction; and if the current kinematic quantity or the engaged friction $\mu$ is greater than the respective first threshold value and said working point is not above said first reference curve, determining that the value of the potential friction is equal to or less than said first reference value $\mu_{p1}$;

providing to an active control system within said vehicle said estimated potential friction as the condition between the tyre and the rolling surface; and assisting, by the active control system, with the driving control of the vehicle based on said estimated potential friction.

2. The method according to claim 1, wherein said first engaged friction/kinematic quantity reference curve corresponds to a reference value $\mu_{p1}$ of potential friction less than or equal to 0.3.

3. The method according to claim 1, wherein said first engaged friction/kinematic quantity reference curve corresponds to a reference value $\mu_{p1}$ of potential friction at least equal to 0.15.

4. The method according to claim 1, wherein said second engaged friction/kinematic quantity reference curve corresponds to a reference value $\mu_{p2}$ of potential friction between 0.35 and 0.5.

5. The method according to claim 1, wherein the first engaged friction threshold value is less than the first reference value $\mu_{p1}$ of potential friction.

6. The method according to claim 1, wherein the first engaged friction threshold value is between 0.05 and 0.2.

7. The method according to claim 1, wherein the second engaged friction threshold value is greater than the first reference value $\mu_p$, of potential friction and less than the second reference value $\mu_{p2}$ of potential friction.

8. The method according to claim 1, wherein the second engaged friction value is between 0.25 and 0.4.

9. The method according to claim 1, wherein both the first and the second predetermined kinematic quantity threshold value and the first and the second predetermined engaged friction threshold value are stored in the memory, and, if the engaged friction is less than the first engaged friction threshold value, and if the current value of the kinematic quantity is less than the first kinematic quantity threshold value, determining that the estimate of the potential friction is not available.

10. The method according to claim 1, wherein both the first and the second predetermined kinematic quantity threshold value and the first and the second predetermined engaged friction threshold value are stored in the memory, and, if the current value of the kinematic quantity is less than the first kinematic quantity threshold value:

if the engaged friction $\mu$ is between said first and said second engaged friction threshold value, determining that the value of the potential friction is greater than said first reference value $\mu_{p1}$ of potential friction; and if the engaged friction $\mu$ is greater than said second engaged friction threshold value, determining that the value of the potential friction is greater than said second reference value $\mu_{p2}$ of potential friction.

11. The method according to claim 10, wherein, if the current value of the kinematic quantity is between the first and the second kinematic quantity threshold value, and if the engaged friction $\mu$ is greater than said second engaged friction threshold value, determining that the value of the potential friction is greater than said second reference value $\mu_{p2}$ of potential friction.

12. The method according to claim 1, wherein both the first and the second predetermined kinematic quantity threshold value and the first and the second predetermined engaged friction threshold value are stored in the memory, and, if the engaged friction is less than the first engaged friction threshold value:

if the current value of the kinematic quantity is greater than the first kinematic quantity threshold value, determining that the value of the potential friction is equal to or less than said first reference value $\mu_{p1}$.

13. The method according to claim 12, wherein, if the engaged friction is between the first and the second engaged friction threshold value, and if the current value of the kinematic quantity is greater than the second kinematic quantity threshold value, and the working point is above said first reference curve, determining that the value of the potential friction is between said first reference value $\mu_{p1}$ and said second reference value $\mu_{p2}$ of potential friction.

14. The method according to claim 1, wherein the active control system comprises an antilock braking system (ABS), and wherein said assisting with the driving control comprises:

selecting, by the ABS, one of a plurality of logics for intervening in braking activity for the vehicle based on the estimated potential friction.

15. The method according to claim 14, wherein said selecting by the ABS occurs before activation of the braking activity.

16. The method according to claim 1, wherein the active control system comprises an advanced driver assistance system.

17. The method according to claim 16, wherein said assisting with the driving control comprises:

controlling a safety distance for the vehicle and providing alarms to the driver based on the estimated potential friction.

18. The method according to claim 16, wherein said assisting with the driving control comprises:

signaling the driver of slippery conditions between the tyre and the rolling surface based on the estimated potential friction.

19. The method according to claim 1, wherein said kinematic quantity is a drift angle α of the tyre and said engaged friction μ is a lateral engaged friction $F_y/F_z$.

20. The method according to claim 19, wherein the first kinematic quantity threshold value corresponds to a drift angle between 0.5° and 1.2°.

21. The method according to claim 19, wherein the second kinematic quantity threshold value corresponds to a drift angle between 1.2° and 2.5°.

22. The method according to claim 19, wherein the working point is determined from values of lateral engaged friction $F_y/F_z$ and drift angle α when the current lateral acceleration of the tyre is greater, in absolute value, than a predetermined lateral acceleration value.

23. The method according to any claim 1, wherein said kinematic quantity is longitudinal slip ε of the tyre and said engaged friction μ is a longitudinal engaged friction $F_x/F_z$.

24. The method according to claim 23, wherein the first kinematic quantity threshold value corresponds to a slip at least equal to 0.5%.

25. The method according to claim 23, wherein the second kinematic quantity threshold value corresponds to a slip at least equal to 0.9%.

26. The method according to claim 23, wherein the working point is determined from values of longitudinal engaged friction $F_x/F_z$ and longitudinal slip ε when a current lateral acceleration of the tyre is less, in absolute value, than a predetermined lateral acceleration value and longitudinal acceleration of the tyre is greater, in absolute value, than a predetermined longitudinal acceleration value.

27. A motor vehicle comprising:
a tyre that, as the motor vehicle travels on a rolling surface, exchanges longitudinal and lateral fores in a plane of contact between the tyre and the rolling surface;
an active control system configured to enhance driving control of the motor vehicle based on a condition between the tyre and the rolling surface;
a memory within the vehicle storing a first and a second predetermined engaged-friction/kinematic quantity reference curve, respectively corresponding to a first and to a second reference value $\mu_{p1}$, $\mu_{p2}$, of potential friction between the tyre and the rolling surface with $\mu_{p2} > \mu_{p1}$; and a first and a second predetermined kinematic quantity threshold value, or a first and a second predetermined engaged friction threshold value; said first threshold value corresponding to a kinematic quantity value or, respectively, engaged friction value where said first reference curve is substantially distinguishable from said second reference curve, and said second threshold value corresponding to a kinematic quantity value or, respectively, engaged friction value where said second reference curve is substantially distinguishable from at least one third reference curve corresponding to a third reference value $\mu_{p3}$ of potential friction with $\mu_{p3} > \mu_{p2}$;
monitoring equipment within the vehicle, comprising an accelerometer positioned on an inner surface of the tyre, configured to detect physical quantities in the tyre rolling along said rolling surface, the physical quantities being correlated to at least one of the longitudinal and lateral forces exchanged in the contact plane between the tyre and the rolling surface, vertical load acting on the tyre, longitudinal slip of the tyre, and drift angle of the tyre;
at least one processor within the vehicle configured to:
determine the engaged friction μ between the tyre and the rolling surface based on the physical quantities detected by the monitoring equipment;
determine a current value of a kinematic quantity between the tyre and the rolling surface based on the physical quantities detected by the monitoring equipment;
determine a current working point given by the engaged friction p and a current value of the kinematic quantity;
compare the current value of the kinematic quantity with the first and the second kinematic quantity threshold value or, respectively, the engaged friction μ with the first and the second engaged friction threshold value; and
estimate the potential friction between the tyre and the rolling surface, wherein:
if the current value of the kinematic quantity or the engaged friction μ is between the respective first and second threshold values and said working point is above said first reference curve, determining that a value of a potential friction is greater than said first reference value $\mu_{p1}$;
if the current value of the kinematic quantity or the engaged friction μ is greater than the respective second threshold value and said working point is above said second reference curve, determining that the value of the potential friction is greater than said second reference value $\mu_{p2}$ of potential friction;
if the current value of the kinematic quantity or the engaged friction μ is greater than the respective second threshold value and said working point is between said first and said second reference curve, determining that the value of the potential friction is between said first reference value $\mu_{p1}$ of potential friction and said second reference value $\mu_{p2}$ of potential friction; and
if the current kinematic quantity or the engaged friction μ is greater than the respective first threshold value and said working point is not above said first reference curve, it is determined that the value of the potential friction is equal to or less than said first reference value $\mu_{p1}$,
wherein the active control system is configured to assist with the driving control of the vehicle based on said estimated potential friction as the condition between the tyre and the rolling surface.

28. The motor vehicle according to claim 27, wherein the active control system comprises an antilock braking system (ABS) configured to select one of a plurality of logics for intervening in braking activity for the vehicle based on the estimated potential friction.

29. The motor vehicle according to claim 27, wherein the active control system comprises an advanced driver assistance system configured to control a safety distance for the vehicle or to signal the driver of slippery conditions between the tyre and the rolling surface based on the estimated potential friction.

* * * * *

UNITED STATES PATENT AND TRADEMARK OFFICE
CERTIFICATE OF CORRECTION

PATENT NO. : 9,746,414 B2
APPLICATION NO. : 14/896092
DATED : August 29, 2017
INVENTOR(S) : Elisabetta Leo et al.

It is certified that error appears in the above-identified patent and that said Letters Patent is hereby corrected as shown below:

On the Title Page

Item (57), Line 5, "$\mu p_1$" should read -- $\mu_{p1}$ --.

In the Claims

Claim 7, Column 21, Line 60, "$\mu_p$," should read -- $\mu_{p1}$ --.

Claim 23, Column 23, Line 16, "The method according to any claim 1" should read -- The method according to claim 1 --.

Claim 27, Column 24, Line 13, "engaged friction p" should read -- engaged friction $\mu$ --.

Signed and Sealed this
Sixth Day of November, 2018

Andrei Iancu
*Director of the United States Patent and Trademark Office*